United States Patent [19]

Carbone

[11] Patent Number: 5,032,133
[45] Date of Patent: Jul. 16, 1991

[54] METHOD AND APPARATUS FOR EXPANDING A SHAFT FOR USE IN PROSTHESIS

[75] Inventor: John J. Carbone, Baltimore, Md.

[73] Assignee: Orthovations, Inc., Baltimore, Md.

[21] Appl. No.: 468,731

[22] Filed: Jan. 23, 1990

[51] Int. Cl.$^5$ .............................................. A61F 2/32
[52] U.S. Cl. .................................................... 623/23
[58] Field of Search ..................... 623/16-23; 606/72, 73, 60, 62-68

[56] References Cited

U.S. PATENT DOCUMENTS

| | | |
|---|---|---|
| 737,555 | 8/1903 | Dorn . |
| 1,152,876 | 9/1913 | Brown . |
| 2,051,251 | 6/1935 | Epstein . |
| 2,280,662 | 9/1940 | Pawsat . |
| 2,486,303 | 4/1948 | Longfellow . |
| 2,719,522 | 7/1952 | Hudack . |
| 3,528,691 | 5/1969 | Matich, Jr. . |
| 3,805,302 | 4/1974 | Mathys . |
| 3,841,774 | 10/1974 | Maxey . |
| 3,846,846 | 11/1974 | Fischer . |
| 3,945,743 | 3/1976 | Koch . |
| 4,078,276 | 3/1978 | Nunes . |
| 4,091,806 | 5/1978 | Aginsky . |
| 4,115,875 | 9/1978 | Rambert . |
| 4,167,047 | 9/1979 | Grundei et al. . |
| 4,520,511 | 6/1985 | Gianezio et al. . |
| 4,530,115 | 7/1985 | Muller et al. . |
| 4,605,350 | 8/1986 | Chater et al. . |

Primary Examiner—David J. Isabella
Attorney, Agent, or Firm—Cushman, Darby & Cushman

[57] ABSTRACT

A prosthetic device includes two or more members having alignable bores and smooth sliding surfaces intercepting the respective bore at an angle; a shaft extending through each bore holds the members in assembled relation with the sliding surfaces abutting one another; rotation of the shaft effects relative sliding motion between the members to vary the width dimension of the device.

22 Claims, 4 Drawing Sheets

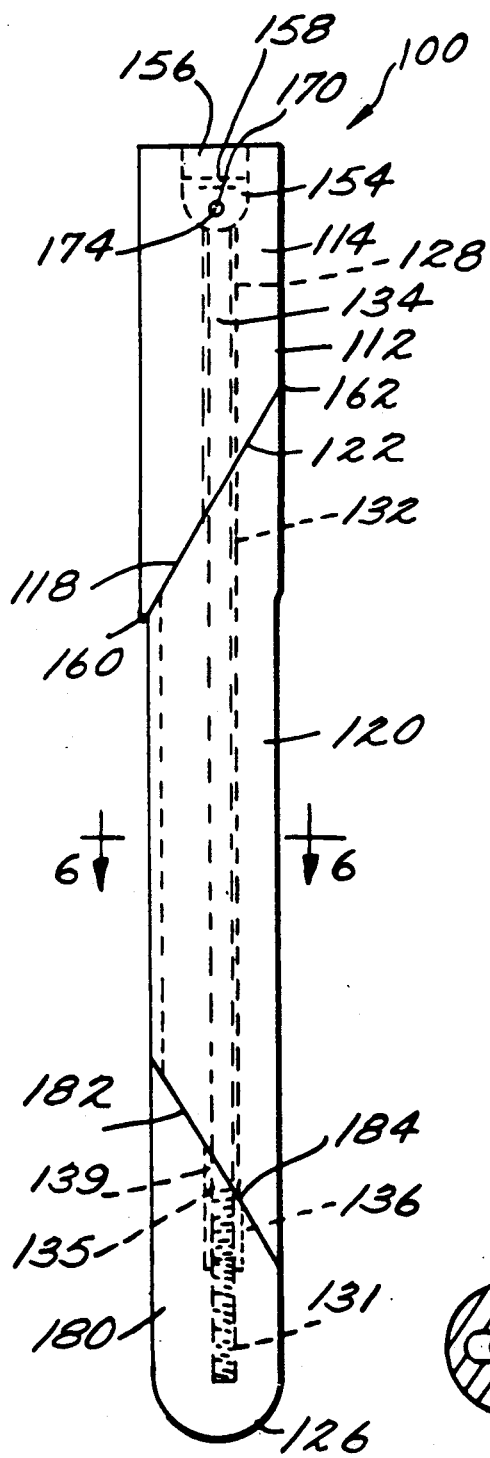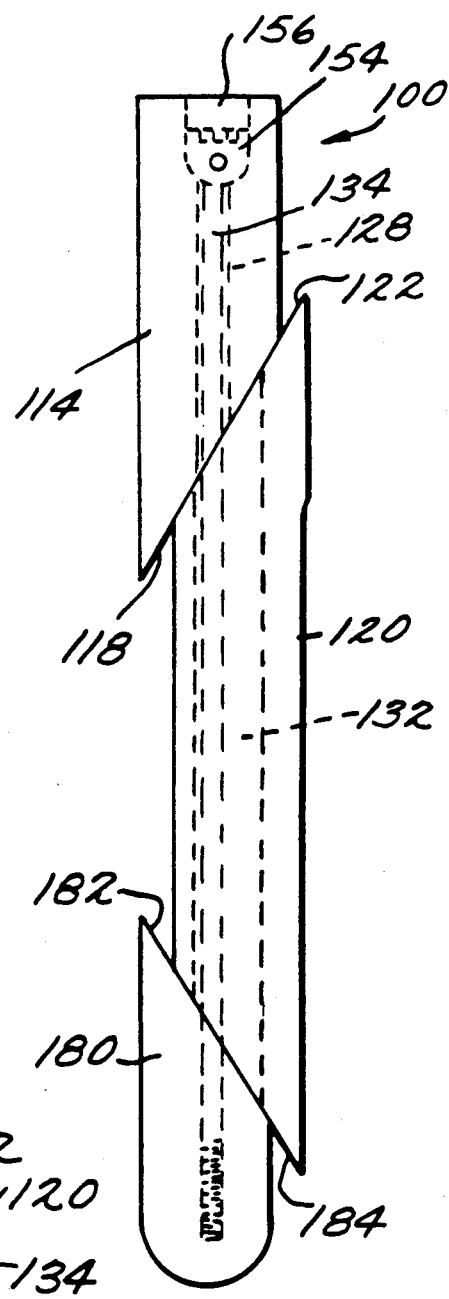
Fig. 4.
Fig. 5.
Fig. 6.

METHOD AND APPARATUS FOR EXPANDING A SHAFT FOR USE IN PROSTHESIS

FIELD OF THE INVENTION

The present invention relates to a device for anchoring a prosthetic member in bone structure and, more particularly, to an anchoring device for use in a hip joint prosthesis and which will minimize, if not eliminate, the imposition of unnecessary stresses on the femur while assuring precise positioning of the prosthesis for cooperation with a compatible socket member.

BACKGROUND OF THE INVENTION

Surgical procedures for replacement of a deteriorated or injured hip joint have employed a number of prosthetic devices which have endeavored to address the problems of ease of use, durability of the prosthesis, adjustment thereof, precision in positioning of the prosthesis as well as preservation of as much of the original bone structure as is practical in light of the extent of the development of arthrosis or of an injury that may have occurred.

In one type of arrangement such as that disclosed in U.S. Pat. No. 4,115,875 a tapered and curved shaft is provided for intramedullary positioning in the femur. While this and similar structures have enjoyed widespread use, they suffer from a number of significant disadvantages. Among these, prominent is the difficulty in anchoring the shaft in place. Under conventional procedures, the shaft has typically been forcibly inserted by the practitioner often with the aid of a mallet or similar tool. The type as well as frequency of damage to the femur has greatly contributed to the failure of this type of prosthesis and complication of the surgical procedure. In addition, the durability of the shaft member, once inserted has not been satisfactory due to the tendency of the shaft to become loose and to move relative to the femoral cavity. In addition, removal of the prosthesis for readjustment or replacement is time consuming and difficult for the patient.

Other devices have attempted to solve the anchoring problem but, in general, these solutions have been at the expense of the integrity of the prosthetic implant, have been difficult to set in place or have imposed concentrated stresses along the length of the femoral cavity thereby resulting in potential damage to the femur. In this connection, reference may be had to U.S. Pat. Nos. 3,846,846, 4,520,511 and 4,530,115.

SUMMARY OF THE INVENTION

It is an object of the present invention to provide a method and device for insertion into a bone structure and which can be precisely positioned and anchored in place much more readily than the devices of the prior art and which will avoid imposing dangerous or uncontrollably concentrated stresses on the bone structure. In addition, the present invention will provide a prosthetic device which will greatly facilitate its insertion into a bone cavity as well as subsequent readjustment for positioning purposes. Further, the device of the present invention will be much more durable in use than many of the devices of the prior art.

In a preferred embodiment, the present invention provides a device for intramedullary insertion and anchoring and comprises two members having elongated abutting surfaces permitting relative sliding motion between the two members upon actuation of a locking device which serves to adjust the positions of the two members relative to one another and to lock the two members in a desired position after insertion into a bone cavity. When assembled, the two members will define a shaft structure which, upon relative movement of the two members in one direction will effect anchoring as a result of substantially radial expansion of the shaft in a bone cavity. In another embodiment, the device of the invention is provided with three members with one of these disposed for relative sliding movement between end members which themselves are movable relative to each other. The locking device serves to retain the three members in the assembled condition as well as to cause, upon actuation, radial expansion and locking once inserted into a bone cavity. With each of these arrangements, the stresses normally imposed on the bone as a result of the anchoring operation will be distributed substantially uniformally over the length of the shaft thereby minimizing or eliminating any undesirable concentration of stresses on the adjacent bone structure.

The foregoing and other advantages will become apparent as consideration is given to the following detailed description taken in conjunction with the accompanying drawings, in which:

BRIEF DESCRIPTION OF THE DRAWINGS

FIG. 4 is a side view in elevation of another embodiment of the invention;

FIG. 5 is a view similar to FIG. 4 but showing the members in their relative positions after expansion;

FIG. 6 is a view along lines 6—6 of FIG. 4; and

DETAILED DESCRIPTION OF THE INVENTION

Figure 1:
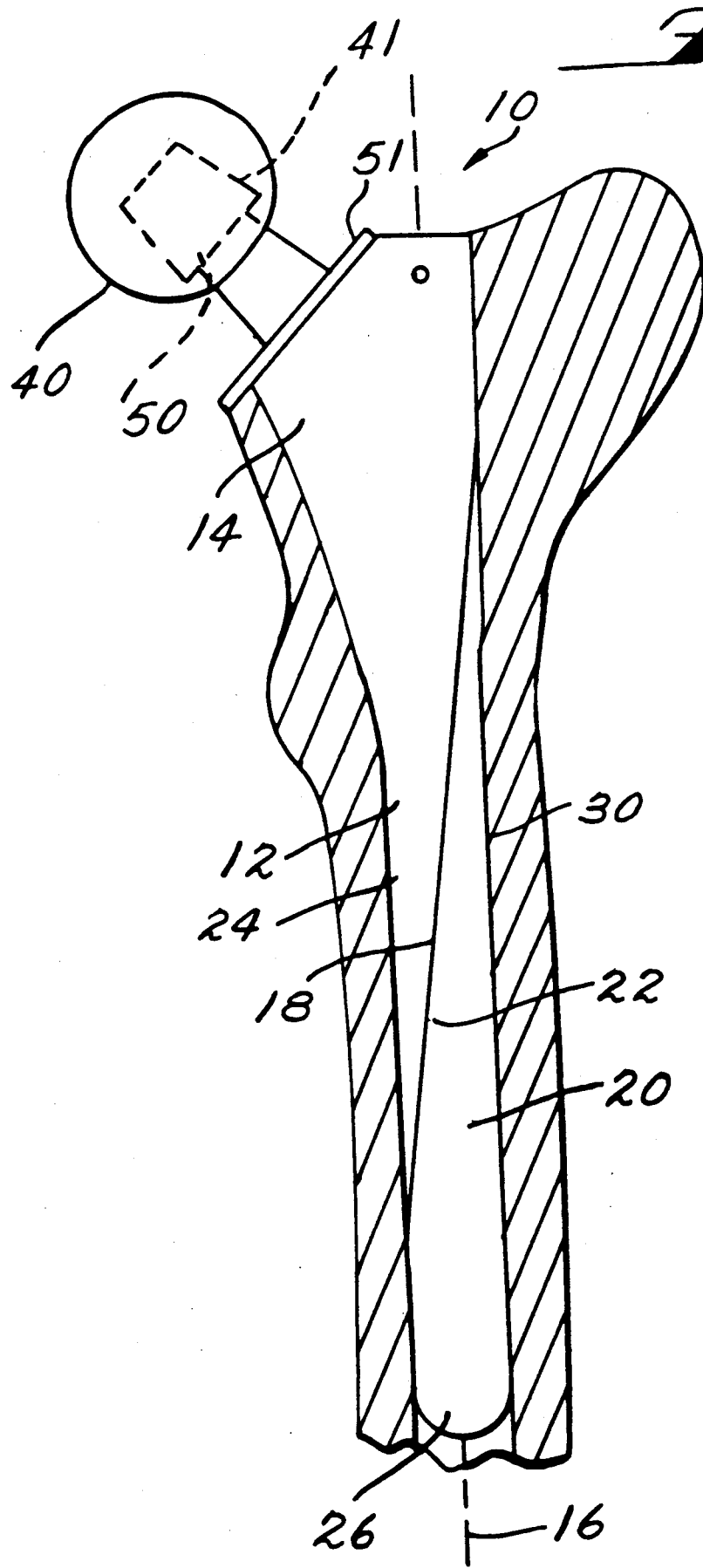
FIG. 1 is a side view in elevation of the device of the present invention.

Referring now to the drawings wherein like numerals designate corresponding parts throughout the several views, there is shown in FIG. 1 an anchoring device 10 of the present invention which, in the illustrated embodiment, is in the form of a hip joint prosthesis. It will be understood that the anchoring device 10 of the present invention may be employed in other surgical procedures which require the anchoring of a device to bone structure.

In the illustrated embodiment, the device 10 is inserted within a femoral canal 30. The ball shaped portion 40 is of a size to be carried within the natural or prosthetic acetabular cavity. As is conventional, the ball portion 40 is provided with a bore 41 for receiving a pin which is preferably in the form of a tapered neck and which extends transversely from a shoulder 51 of the device 10.

The body of the device 10 includes a first member 12 having an enlarged end 14 for the purpose of providing structural support for the neck 50 which is formed to extend at an angle to the axis 16 of the device 10. The member 12 opposite its end 14 has an abutment surface 18 which extends at an angle to the axis 16 of the device 10. The second member 20 of the device is provided with a surface 22 complementary to surface 18. The exterior configuration of the end portion 24 of member 12 and member 20 along approximately two thirds of the axis 16 remote from the end 14 will define a substantially cylindrical shaft body when in the assembled position illustrated in FIG. 1. The distal end 26 of the member 20 may be either smoothly rounded, as illustrated, or pointed to facilitate insertion into the femoral cavity.

Figure 2:
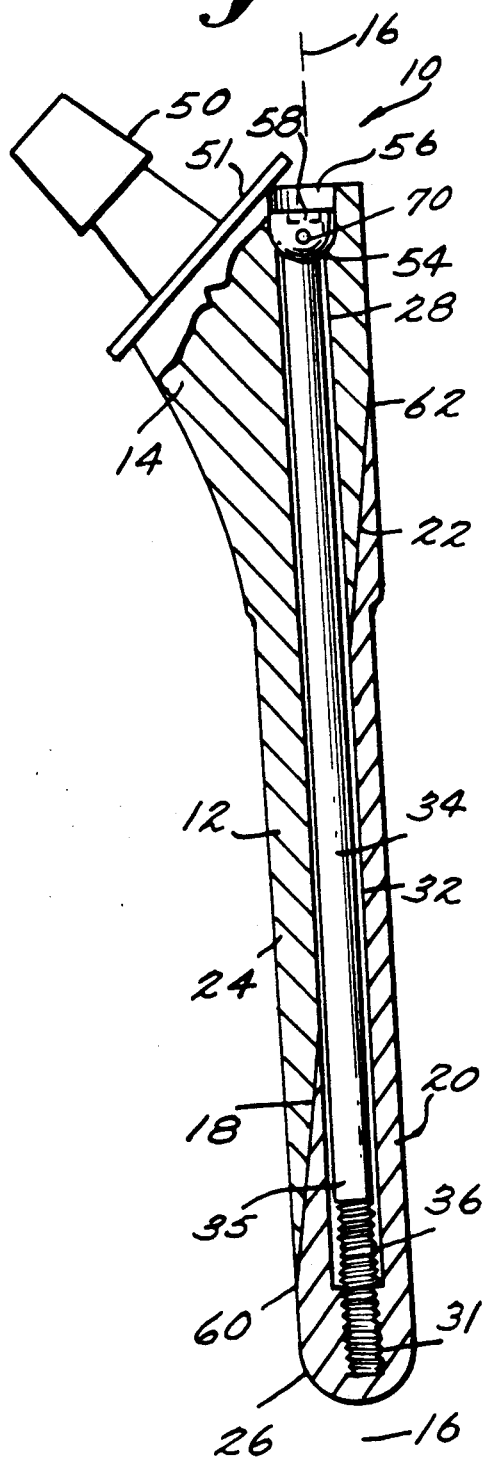
FIG. 2 is a sectional view along lines 2—2 of FIG. 1.

With reference now to FIG. 2, there is shown a sectional view of the device 10 of FIG. 1 looking transverse to the axis 16. Member 12 has an internally formed through bore 28 which opens onto slide surface 18 in an elongated manner due to the angular interception of the surface 18 with the bore 28. Similarly, member 20 is provided internally with a bore 32 which opens onto face 22 in the same manner. Together the bores 28 and 32 form an internal cavity through which extends manipulating means in the form of a locking shaft 34 which at its end 35 is provided with a reduced diameter threaded extension 36 which is received in a threaded bore 31 in member 20. The opposite end of the shaft 34 is provided with an enlarged head 54 having a hemispherically shaped peripheral surface or wall and which is received in a bore 56, the inner end of which is also hemispherically shaped to complement the surface of the head 54 for reasons which will be discussed below. The exposed end of the head 54 is provided with a tool receiving recess 58 which may be hexagonal to facilitate cooperation with a mating tool to effect rotation of the shaft 34.

In use, once the receiving cavity in the femur has been prepared, the practitioner will insert the device 10 with the members 12 and 20 positioned so that the device will exhibit the minimum peripheral circumference. Typically, the cavity will have been prepared by drilling to the appropriate depth and diameter. In using the device 10 of this invention, it is preferable that the diameter of the femoral cavity be enlarged to a size only slightly larger than the minimum diameter of the assembled device 10 so as to permit manual insertion by the practitioner.

Once a device 10 is properly positioned, the user will then rotate the shaft 34 by insertion and rotation of the appropriate tool into recess 58. By rotation of the shaft 34 in one direction, the threaded interconnection between the extension 36 of shaft 34 and bore 31 will effect movement of member 20 toward end 14 of the device 10 thereby effecting a substantially uniform radial expansion of the device 10 between the points 60 and 62 along axis 16. Preferably, and depending on the precision of the drilling operation, the expansion required to effect secure anchoring will only be on the order of several millimeters or up to about 10 millimeters. In such circumstances, the material of the shaft 34 should normally be sufficiently resilient to easily tolerate the deflection caused by the relative sliding movement along surfaces 18 and 22 of members 12 and 20.

In some circumstances, particularly where larger relative motion between members 12 and 20 is required, the present invention will readily accommodate the deflection of the shaft 34 by the provision of the spherical interface between the head 54 and the lower end of bore 56. To this end, the interior diameter of the bores 28 and 32 are selected to provide a sufficient space between the internal surfaces of the bores 28 and 32 and the exterior diameter of the shaft 34. With this arrangement, as the member 20 moves upwardly as viewed in FIG. 2, the shaft 34 is free to pivot from its spherical head 54 to the desired extent to relieve any stress that normally would result from the relative movement of members 12 and 20.

Figure 3A:
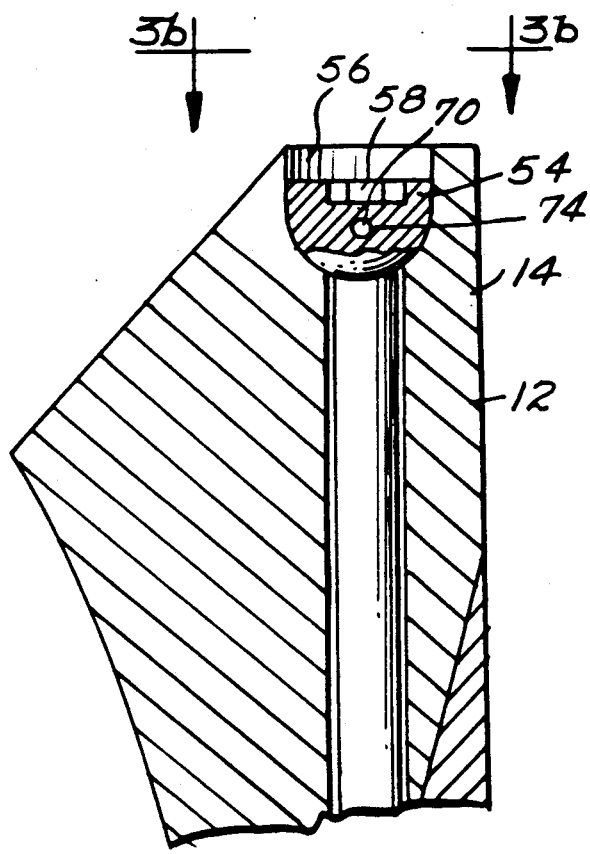
FIG. 3A is an enlarged detail view of the locking member of the device of the present invention and FIG. 3B is a view along lines 3b—3b of FIG. 3A.
Figure 3B:
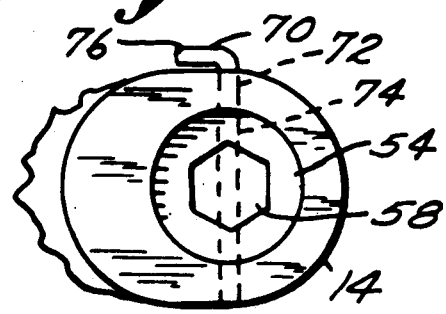

With reference to FIGS. 3A and 3B, subsequent to the foregoing operation, further rotation of the shaft 34 may be prevented by the insertion of a locking pin 70 through a bore 72 provided adjacent the end 14 with the pin extending into an opening 74 formed in the head 54. A plurality of such openings 74 may be provided circumferentially spaced about the head 54 to accommodate various angular positions of the head 54 relative to the bore 72. The pin 70 may be bent at 76 to hold it in place and it will apparent to those skilled in this art that other devices for locking the shaft 34 in place may be employed.

From the foregoing, it will be apparent that adjustment as well as repositioning of the device 10 can be readily accomplished simply by unlocking the head 54 and reverse rotation thereof to effect reduction in the external circumference of the assembled members 12 and 20.

With reference now to FIGS. 4–6, there is shown another embodiment 100 of the present invention where corresponding parts are referred to using numerals corresponding to the previous embodiment but raised by 100.

As shown in FIG. 4, the device 100 includes three members 114, 120 and 180. As will be apparent, the structure and operation of members 114 and 120 will be the same as described above in connection with the embodiment of FIGS. 1-3B. It will be noted, however, that sliding surfaces 118 and 122 intersect bores 128 and 132 at selected angles. Intermediate member 120 is provided with a bore 132 of increased width dimension as shown in FIG. 6 for reasons to be described below.

The intermediate member 120 is provided with a sliding surface 184 to complement a sliding surface 182 provided on the proximal end of the member 180. Also, the distal member 180 is provided with the threaded bore 131 in which is received the threaded end 136 of shaft 134 which extends entirely through the bore 132 of intermediate member 120. Lastly, it will be noted that the sliding surfaces 182 and 184 intercept their respective bores 132 and 139 at the same angle as surfaces 128 and 122 intercept bores 132 and 128 but rotated so as to extend in a complementary manner to surfaces 118 and 122. It will be apparent that the angles of interception may be different where it is useful to achieve relatively different expansion rates and which may impose correspondingly different forces. For example, in some patients, a portion of the femoral cavity may be substantially wider proximally than distally. In such a case, it will be useful to form the angle of interception of the surfaces 118 and 122 with the bores 128 and 132 with a much greater angle than the angle of interception of the surfaces 182 and 184 with their corresponding bores. With this modification, for a selected rotation of the shaft 134, member 112 will move laterally a greater distance than member 180. This will minimize or even eliminate the tendency of the device 100 to pivot in the femoral cavity about a site near the ball member where the device 100 is used in a hip prosthesis.

Operation of the shaft 134 by rotation of head 154 is the same as in the previous embodiment except, with the structure of the embodiment of FIGS. 4–6, movement of the distal member 180 upon rotation of the shaft 134 will effect movement of the intermediate member 120 as a result of shifting of member 180 along the axis of shaft 134 towards member 114. Locking of the members in the position as illustrated in FIG. 5 is effected also in the same manner as in the previous embodiment.

By making the bore 132 of the intermediate member 120 of greater width, as shown in FIG. 6, a substantially greater latitude in radial expansion of the device 100 can be achieved. In addition, axial misalignment of a bone cavity can be tolerated as the degree to which the shaft 134 is deflectable is increased. The shaft, when the device is in the locked condition, in a cavity, will normally not be a load bearing member as the loads will be transmitted substantially through the surfaces 118, 122, 182 and 184 and the associated members 114, 120 and 180.

Figure 7:
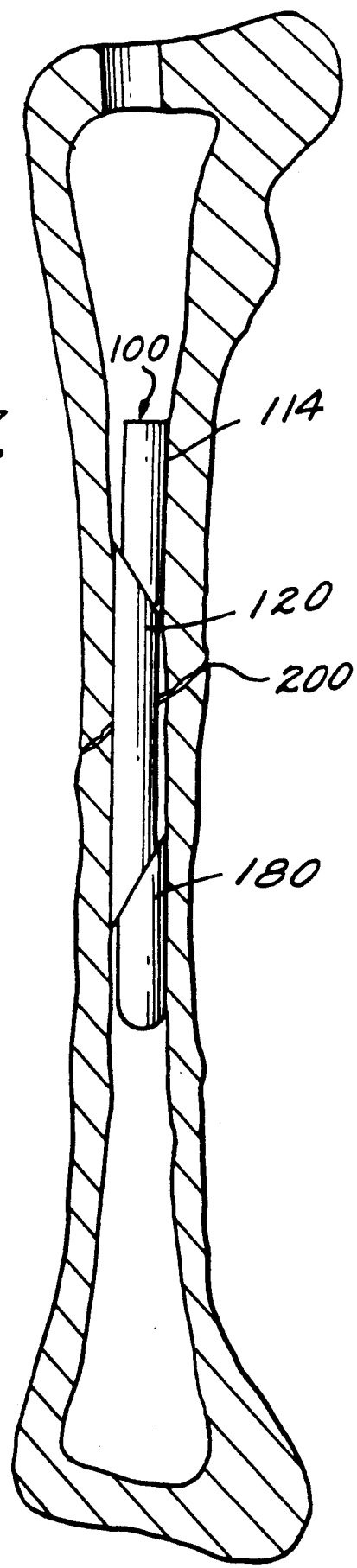
FIG. 7 is a view of the locking device of FIGS. 4-6 in one example of use.

The embodiment 100 of the present invention is particularly useful in securing together pieces of a broken bone particularly where the break is a spiral fracture or comminuted fracture. In these types of fractures, the device 100 would be used by insertion in the bone cavity to an extent to traverse the fracture as shown in FIG. 7 where the device 100 is installed so as to straddle the site of a break 200. Also as shown, the intermediate member 120' may be slightly curved to facilitate placement of the device about the break and allows more secure locking of the device in place. The practitioner would then secure the device 100 in place by effecting the relative shifting of the members, as described above, but with an extended length tool to thereby immobilize the fracture fragments in the desired position. In insertion of the device 100, the ability of the member 180 to shift laterally relative to the member 114 will also allow the device to compensate for the natural curvature of the bone cavity, where necessary.

It will also be apparent to those skilled in this art that the device of the present invention may be employed to effect other types of surgical procedures where it is desired, for example, to join broken diseased or deformed bones or portions thereof by the use of a structure of the present invention having different overall relative dimensions compared to that which would be employed in the illustrated embodiments.

Having described the invention, it will be apparent that various other modifications may be made thereto without departing from the spirit and scope of this invention as defined in the appended claims.

What is claimed is:

1. A prosthetic positioning device adapted for cooperation with an interior surface of a bone cavity, the positioning device comprising separate first and second elongated members, said first member having an elongated bore extending therethrough from one end to an opposite end, said second member having an elongated bore extending therethrough from one end to at least adjacent an opposite end, said opposite end of said first member and said one end of said second member being disposed to face each other and having end surfaces extending at acute angles to said respective bores to form a slide surface with said angles being substantially equal, said positioning device further including an elongated actuatable manipulation means configured to be disposed within said bores for holding said slide surfaces in abutting relation to one another and upon actuation of said manipulation means causing relative sliding motion between said first and second members along the slide surfaces thereby varying at least a width dimension of the positioning device.

2. The invention as claimed in claim 1 wherein said opposite end of said second member is closed and said bore adjacent said closed opposite end is formed with a threaded bore portion and said manipulation means comprises a shaft having diameter less than the diameter of said bores of said first and second members, said shaft having a threaded end engaged in said threaded bore portion whereby rotation of said shaft in one direction will effect said sliding motion to increase the width dimension of said positioning device in the area where said slide surfaces overlap said shaft and rotation of said shaft in a direction opposite said one direction will effect said sliding motion to decrease said width dimension.

3. The invention as claimed in claim 1 wherein said manipulation means is a shaft extending along said bores of said first and second members with said shaft being threadably engaged with one of said bores so that rotation of said shaft will effect said sliding motion.

4. The invention as claimed in claim 2 wherein said bore of said first member at said one end of said first member is formed with a counter-bore at least a portion of which has a diameter larger than the diameter of said bore of said first member, said shaft having a head portion received in said counter-bore.

5. The invention as claimed in claim 4 wherein said counter-bore has a curved inner wall surrounding said bore of said first member and said head portion of said shaft has a curved surface surrounding said shaft and mating with said curved inner wall of said counter-bore, said bores of said first and second members having a diameter greater than the diameter of said shaft so that, upon occurrence of said sliding motion, said shaft is pivotable on said head portion.

6. The invention as claimed in claim 4 wherein said head portion has recess means for cooperation with tool means for rotating said head portion and shaft.

7. The invention as claimed in claim 4 wherein said one end of said first member and said head portion have removable, interchangeable locking means for preventing rotation of said shaft.

8. The invention as claimed in claim 1 wherein said first member includes a shoulder portion having neck means for cooperation with a hip joint ball member with said neck means extending at an angle to said bore of said first member.

9. A prosthetic positioning device as claimed in claim 1 further including a neck extending from said first elongated member wherein said neck is configured for insertion into complementary recess means of a hip joint ball member.

10. A prosthetic positioning device adapted for cooperation with an interior surface of a bone cavity, the positioning device comprising separate first, second and third elongated members, said first member having an elongated bore extending therethrough from one end to an opposite end, said second member having an elongated bore extending therethrough from one end to an opposite end, said third member having an elongated bore extending therethrough from one end to at least adjacent an opposite end, said opposite end of said first member and said one end of said second member being disposed to face each other and having end surfaces extending at acute first angles to said respective bores to form a first slide surface with said first angles being substantially equal, said opposite end of said second member and said one end of said third member being disposed to face each other and having end surfaces extending at acute angles to said respective bores to form a second slide surface with said second angles being substantially equal, said positioning device further including an elongated actuatable manipulation means configured to be disposed within said bores for holding said slide surfaces in abutting relation to one another and upon actuation of said manipulation means causing relative sliding motion between said first and third members and said second member along said slide surfaces thereby varying at least a width dimension of the positioning device.

11. The invention as claimed in claim 10 wherein said opposite end of said third member is closed and said bore of said third member adjacent said closed opposite end is formed with a threaded portion and said manipulation means comprises a shaft having a diameter less than the diameter of said bores of said members, said shaft having a threaded end engaged in said threaded portion whereby rotation of said shaft in one direction will effect said sliding motion to increase the width dimension of said positioning device in the area where said first and second slide surfaces overlap said shaft and rotation of said shaft in a direction opposite said one direction will effect said sliding motion to decrease said width dimension.

12. The invention as claimed in claim 10 wherein said manipulation means is a shaft extending along said bores of said members with said shaft being threadedly engaged with said bore of said third member so that rotation of said shaft will effect said sliding motion.

13. The invention as claimed in claim 11 wherein said bore of said first member at said one end of said first member is formed with a counter-bore at least a portion of which has a diameter larger than the diameter of said bore of said first member, said shaft having a head portion received in said counter-bore.

14. The invention as claimed in claim 13 wherein said counter-bore has a curved inner wall surrounding said bore of said first member and said head portion of said shaft has a curved surface surrounding said shaft and mating with said curved inner wall of said counter-bore, said bores of said members having a width dimension greater than the diameter of said shaft so that, upon occurrence of said sliding motion, said shaft is pivotable on said head portion.

15. The invention as claimed in claim 13 wherein said head portion has recess means for cooperation with tool means for rotating said head portion and shaft.

16. The invention as claimed in claim 13 wherein said one end of said first member and said head portion have removable, interchangeable locking means for preventing rotation of said shaft.

17. The invention as claimed in claim 10 wherein said first member includes a shoulder portion having neck means for cooperation with a hip joint ball member with said neck means extending at an angle to said bore of said first member.

18. The invention as claimed in claim 10 wherein said third member is curved from said one end to said opposite end.

19. A method of treating a bone having a break or fracture at a site on the bone and where the bone has an interior cavity with a positioning device including separate first and second elongated members, said first member having an elongated bore extending therethrough from one end to an opposite end, said second member having an elongated bore extending therethrough from one end to at least adjacent an opposite end, said opposite end of said first member and said one end of said second member being disposed to face each other and having end surfaces extending at acute angles to said respective bores to form a slide surface with said angles being substantially equal, said positioning device further including an elongated actuatable manipulation means configured to be disposed within said bores for holding said slide surfaces in abutting relation to one another and upon actuation of said manipulation means causing relative sliding motion between said first and second members along the slide surfaces thereby varying at least a width dimension of the positioning device, the steps comprising opening the cavity, removing tissue from the cavity, inserting said positioning device into said cavity to a depth so that a portion of the positioning device extends beyond the site, actuating said manipulation means to cause said relative sliding motion to increase the width dimension of said positioning device to thereby lock the positioning device against the interior surface of the cavity to thereby hold the bone in a fixed position relative to said positioning device.

20. The method as claimed in claim 19 including the step of locking said manipulation means to prevent further actuation thereof subsequent to said actuating step.

21. A method of treating a bone having an interior cavity and a break or fracture at a site thereon with a positioning device of the type including separate first, second and third elongated members, said first member having an elongated bore extending therethrough from one end to an opposite end, said second member having an elongated bore extending therethrough from one end to an opposite, said third member having an elongated bore extending therethrough from one end to at least adjacent an opposite end, said opposite end of said first member and said one end of said second member being disposed to face each other and having end surfaces extending at acute angles to said respective bores to form a first slide surface with said first angles being substantially equal, said opposite end of said second member and said one end of said third member being disposed to face each other and having end surfaces extending at acute second angles to said respective bores to form a second slide surface with said second angles being substantially equal, said positioning device further including an elongated actuable manipulation means configured to be disposed within said bores for holding said slide surfaces in abutting relation to one another and upon actuation of said manipulation means causing relative sliding motion between said first and third members and said second member along said slide surfaces thereby varying at least a width dimension of the positioning device, the steps comprising opening the cavity, removing tissue from the cavity, inserting said positioning device into said cavity to a depth so that said second member extends along the site, actuating said manipulation means to cause said relative sliding motion to increase the width dimension of said positioning device to thereby lock the positioning device against the interior surface of the cavity to thereby hold the bone in a fixed position relative to said positioning device.

22. The method as claimed in claim 21 including the step of locking said manipulation means to prevent further actuation thereof subsequent to said actuating step.

* * * * *